United States Patent [19]
Reid

[11] Patent Number: 5,626,397
[45] Date of Patent: May 6, 1997

[54] ADULT PASSIVE RESTRAINT APPARATUS AND METHOD OF PASSIVE RESTRAINT

[76] Inventor: Laura A. Reid, 764 8th Ave. S.E., Hickory, N.C. 28602

[21] Appl. No.: 514,680

[22] Filed: Aug. 14, 1995

[51] Int. Cl.[6] .................................................. A62B 35/00
[52] U.S. Cl. .......................... 297/467; 297/485; 297/229
[58] Field of Search ............................... 297/229, 228.1, 297/228, 225, 467, 485

[56] References Cited

U.S. PATENT DOCUMENTS

| | | |
|---|---|---|
| 1,538,538 | 5/1925 | Wood . |
| 2,652,183 | 9/1953 | Hlivka . |
| 3,604,750 | 9/1971 | Doering . |
| 4,188,065 | 2/1980 | Meeker . |
| 4,235,474 | 11/1980 | Rosenberg . |
| 4,871,210 | 10/1989 | Alexander et al. . |
| 5,042,878 | 8/1991 | Collins . |
| 5,275,463 | 1/1994 | Rocha . |
| 5,297,852 | 3/1994 | Morales-Quintero . |

Primary Examiner—Peter M. Cuomo
Assistant Examiner—Stephen Vu
Attorney, Agent, or Firm—Allen, Dyer, Doppelt, Milbrath & Gilchrist, P.A.

[57] ABSTRACT

A passive restraint apparatus and method of passive restraint are provided for supporting a user, i.e., preferably an adult, in a substantially upright seated position so as to enable the user to maintain free upper torso movement. The restraint apparatus includes an upper back section for extending along the back section of a chair or wheelchair, a seat section for extending beneath a user's lower torso along a seat of the chair, a lower leg section for extending beneath a user's lower legs, and a lower torso panel for extending between a user's legs and securing about the back of the chair. The restraint apparatus supports the user in an upright seated position, supports the user's feet from dangling off of the foot supports of a wheelchair, and can readily be obscured while in use by covering it with a blanket or the like. The restraint apparatus can also function as a stretcher for the transporting of fragile or uncooperative people from the chair to another location and minimizing the risk of injury to the person and the transporters.

8 Claims, 5 Drawing Sheets

ADULT PASSIVE RESTRAINT APPARATUS AND METHOD OF PASSIVE RESTRAINT

FIELD OF THE INVENTION

The present invention relates to an apparatus for passively restraining an adult in a seated position. More specifically, the invention relates to an apparatus for supporting an adult in a substantially upright position or reclined position in a chair, to provide a secure feeling to the person while enabling essentially unhindered movement of the person's upper body.

BACKGROUND OF THE INVENTION

As a result of the aging process, injuries and the like, many adults are unable to easily support themselves in a seated position. Discomfort while sitting and an inability to support and maintain themselves in an upright position can represent significant problems for many individuals, particularly those confined to wheelchairs, for a variety of reasons. For example, conventional wheelchairs typically have a flexible vinyl or fabric-type seat in order that the wheelchair can be folded for storage and transport. As a result, the seat typically fails to provide much support for the user's lower torso, which in turn makes it difficult for the user to maintain an upright seated position for extended periods of time. In addition, the edge of the foldable seat can cut into the underside of the user's legs, particularly as the user's weight bears down on the seat for extended periods of time.

In addition, conventional wheelchairs typically have foot supports which fold down to extend beneath the feet of the wheelchair user. When a wheelchair user slumps or slides forward in the wheelchair seat, the user typically has to try to push his or her feet against these foot supports to try to scoot their lower torso rearward in the seat. Because these foot supports are typically flimsy, this "pushing off" can be difficult if not impossible for many to perform, and particularly difficult for the elderly. In addition, it is often difficult for the wheelchair user to maintain his or her feet on these foot supports, and the user's feet may dangle off of the pedals. As a result, the user's feet can fall in the path of the wheelchair as it is being pushed, drag along the ground, and/or interfere with the motion of the wheelchair and potentially cause injury to the user.

Geriatric chairs are often used in lieu of conventional wheelchairs in nursing homes and the like, because they provide greater support for those patients that need to remain in the seats for extended periods of time. In addition, geriatric chairs typically can be made to assume a variety of positions and include a portion which provides support to the patient's legs. These chairs, however, typically have fold-down foot supports which extend from the patient leg support portion of the chair. When the foot support is positioned in its foot supporting position, however, a substantial space typically exists between the leg support and foot support. Therefore, patients tend to get their feet caught in this space, which can cause injuries and substantial discomfort, as well as interfere with the movement of the chair.

An additional problem faced, particularly in many health care facilities, is the transport of the infirm from a chair to a bed, stretcher, car seat or the like. Many patients are in such a fragile state that the simple firm gripping of their appendages by another can result in pain and bruising. Additionally, as a result of discomfort and a decline in their mental faculties, patients often struggle during their transport which can cause injuries to themselves and others.

Attempts have been made to assist in supporting and restraining people in seated upright positions. For example, U.S. Pat. No. 5,042,878 to Collins describes a restraint for securing an invalid in a chair or wheelchair. The restraint includes a back section for releasable securement to the back of a chair, and an integral seat section for extending beneath the user's buttocks. The seat section terminates in a crotch strap which extends between the legs of the user and is secured around the wearer's torso and chair by way of a torso strap. The back section includes a pair of openings proximate its upper end in order that they can threadingly receive the handlebars of a wheelchair or upright members of a chair. Because the restraint fails to extend beyond the seat portion of the chair, it does not provide any support for a wearer's feet. Further, because the restraint is adapted to be threaded over the chair, the user must be removed from the restraint before it can be removed from the chair or wheelchair to which it is attached.

Similarly, U.S. Pat. Nos. 5,297,852 and 3,604,750 to Morales-Quintero and Doering, respectively, describe restraints for supporting enfeebled individuals in a seated position in a wheelchair. The device of the Morales-Quintero patent includes front and rear panels joined by a crotch portion which extends between the user's legs. The rear panel extends beneath the user's buttocks on the wheelchair seat, and elongated straps are secured to the front panel for extending about a user's upper torso. The Doering restraint likewise includes seat, back and crotch portions, and upper torso straps. Because these restraints bind the user's shoulders, they can tend to be uncomfortable to some users and unduly restrictive of the user's movements. Additionally, because these upper torso restraints are readily visible to others, they can be a source of embarrassment to those users whose mental faculties remain intact, and the great degree of movement restriction can be a significant source of anxiety to the user. Further, because these restraints do not extend beyond a user's crotch region, they fail to assist in the support of the lower portion of a user's body.

Thus, a need exists for a restraint apparatus for the infirm, particularly the adult infirm, which supports the infirm person in an upright seated position while enabling the person to maintain free upper torso movement. In addition, a need exists for a restraint apparatus which facilitates the maintenance of a wheelchair or geriatric chair user's feet on the chair foot supports, and for facilitating the transport of a fragile or uncooperative patient from a chair to a bed or the like.

OBJECTS AND SUMMARY OF THE INVENTION

With the foregoing in mind, it is an object of the present invention to provide a passive restraint apparatus and method for use in combination with a chair, wheelchair, geriatric chair, automobile seat, or the like for maintaining a user in an upright seated position.

It is also an object of the present invention to provide an adult passive restraint apparatus for supporting a user's lower legs and feet which assists in maintaining the user's feet on the foot supports of a wheelchair, geriatric chair, or the like.

It is a further object of the present invention to provide a restraint apparatus for maintaining a user in an upright seated position and for assisting in the transport of an infirm or uncooperative person to a different location while minimizing the risk of injury to the person and those assisting in the transport process.

It is another object of the present invention to provide a restraint apparatus which covers only minimal portions of a person's body, thereby enabling its appearance to be minimized or obscured as desired by the user, by covering it with a blanket or the like, and to support the user sufficiently to allow him to feel secure without feeling restrained.

These and other objects are accomplished through the provision of a passive restraint apparatus having a back section for positioning on and securement to the back of a chair, wheelchair, geriatric chair, or the like, a seat section for extending beneath a user's lower torso on the seat of the chair, a lower leg section for extending beneath the lower legs and preferably the feet of the user, and a lower torso panel for extending between the user's legs and securement about the user's torso and to the chair to thereby support the user in an upright position. The back, seat and lower leg sections preferably are integrally attached in order that they are provided in the form of a single elongate body panel.

The restraint apparatus preferably includes an upper pocket which is sized and configured to extend over the chair back to support the restraint apparatus thereon. This upper pocket preferably extends across the full width of the elongate body panel. The upper pocket preferably has sufficient size to enable it to extend over the handles of a wheelchair or headrest of an automobile seat as well as the chair back, as this enables the restraint apparatus to selectively be used in combination with a chair, wheelchair, geriatric chair and car seat. In addition, because of its enlarged size, the upper pocket can be readily removed from the headrest or wheelchair handles so that the restraint apparatus can be used as a stretcher, as discussed further infra.

The restraint apparatus also includes a lower pocket for extending over the foot supports, where applicable, of a wheelchair, geriatric chair, recliner, or the like, to secure the lower leg section of the restraint apparatus in its desired position behind the user's lower legs and preferably underneath the feet. The lower leg section can thus cradle and maintain the wearer's feet on the foot supports of the chair. In this way, the user's comfort is not only enhanced by the additional support provided, but in the case of a moving chair such as a wheelchair or geriatric chair, the risk of injury is reduced. Specifically, the risk of the user's feet falling from the foot supports and into the path of the chair while it is being moved is minimized due to the support provided thereby providing protection for the user. Further, because the seat and leg sections of the restraint apparatus extend over the edge of the seat of the chair to which they are secured, they tend to minimize the degree to which the seat edge cuts into the back of the wearer's legs.

The restraint apparatus further includes a plurality of pairs of mating straps which are designed to be secured to the chair, preferably in encircling fashion, for securing the restraint apparatus thereon. In a preferred form of the invention, the mating straps forming each pair are part of a single long piece of strap material. The piece of strap material can be sewn or otherwise attached so that it extends across the width of the elongate body panel, and beyond the opposite sides of the panel. In this way, the straps also provide additional support for the restraint apparatus which is particularly desirable when the restraint apparatus is used in the manner of a stretcher as discussed in more detail below.

The lower torso panel preferably has a first end which is secured to the elongate body panel, preferably to a central portion thereof. The end of the lower torso panel which is secured to the elongate body panel is preferably relatively narrow in order to extend comfortably through a user's legs. The lower torso panel preferably tapers outwardly to a relatively wider upper end. Ideally, this relatively wider end is substantially free of constraints so that it can be moved in a hinged manner about the point of securement of the lower torso panel to the elongate body panel. In this way, the lower torso panel can be made to hang in a direction towards a user's feet while the user is being seated in the chair and then brought upwardly over the user's lower torso. The lower torso panel includes straps which extend outwardly from its upper end and preferably include mating releasable fasteners which enable the straps to be secured together so that the lower torso portion encircles the user and the chair to which the user is being secured. In this way, a user can be supported in an upright seated position while upper torso movements of the user remain virtually unrestricted.

Because the leg section of the restraint apparatus extends beneath substantially the full extent of a user's legs, the restraint apparatus can be used to transport a user to another location or to a reclined position, in a manner similar to a stretcher. To move the person, the transporters need only disengage the straps from their secured position about the chair and then grab opposite sides of the restraint apparatus to lift the person seated thereon. In this way, the person can be lifted without discomfort and cradled in the restraint apparatus. Further, should the person become uncooperative and attempt to kick or struggle, the transporters need only bring the opposite sides of the restraint apparatus more closely together. Because the weight of the person in the restraint apparatus will bear down on the restraint apparatus, the person will be effectively enveloped in the restraint apparatus in a cocoon-like manner and will be unable to kick or otherwise injure the transporters. In a preferred form of the invention, the pairs of mating straps which are secured to the elongate body panel are of sufficient length that they can be grasped by or wrapped around the hands of the transporters to aid in their transport of a person on the restraint apparatus. The restraint apparatus can also be provided with other types of handles to assist in the transport of a person on the restraint device.

The present invention also includes a method for passively restraining a patient in a seated and upright position. The method preferably includes positioning an elongate body panel so as to extend over a back portion, a seat portion, and a lower leg portion of a chair. A lower pocket connected to the lower end portion of the elongate body panel is positioned so as to extend over the lower end portion of the chair. The method also includes positioning a patient on the elongate body panel in the chair and securing the patient to the chair by positioning a lower torso panel connected to the elongate body panel such that a first end of the lower torso panel is secured to the elongate body panel between the patient's legs and a second end is secured around the lower torso of the patient and to the chair proximate the back section of the restraint apparatus to thereby support the patient within the chair.

BRIEF DESCRIPTION OF THE DRAWINGS

Other objects and advantages will appear as the description proceeds when taken in connection with the accompanying drawings, in which.

DETAILED DESCRIPTION

The present invention now will be described more fully hereinafter with reference to the accompanying drawings, in which preferred embodiments of the invention are shown. This invention, however, may be embodied in many different forms and should not be construed as limited to the illustrated embodiments set forth herein; rather, these illustrated embodiments are provided so that this disclosure will be thorough and complete, and will fully convey the scope of the invention to those skilled in the art. Like numbers refer to like elements throughout.

As illustrated in FIGS. 1–5, a restraint apparatus 10 is provided which is adapted to be secured to a chair or wheelchair W, geriatric chair G, or the like and which is designed to support a user in a substantially upright seated position within the chair. The restraint apparatus 10 is preferably in the form of an elongate body panel 12 which includes a back section 12A, a seat section 12B, and a leg section 12C. These sections 12A, 12B, and 12C are preferably formed as one integral piece, though they can be formed as separate elements and secured together to form the elongate body panel 12. The elongate body panel 12 is preferably substantially rectangular-shaped, as this shape has been found to accommodate chairs many different varieties and shapes. The elongate body 12 also desirably has rounded corners, as this provides a neat, aesthetically appealing appearance and does not present any sharp corners of excess material extending from the elongate body panel. However, it is noted that a variety of elongate body panel shapes can be used, while remaining within the scope of the present invention.

Figure 1:
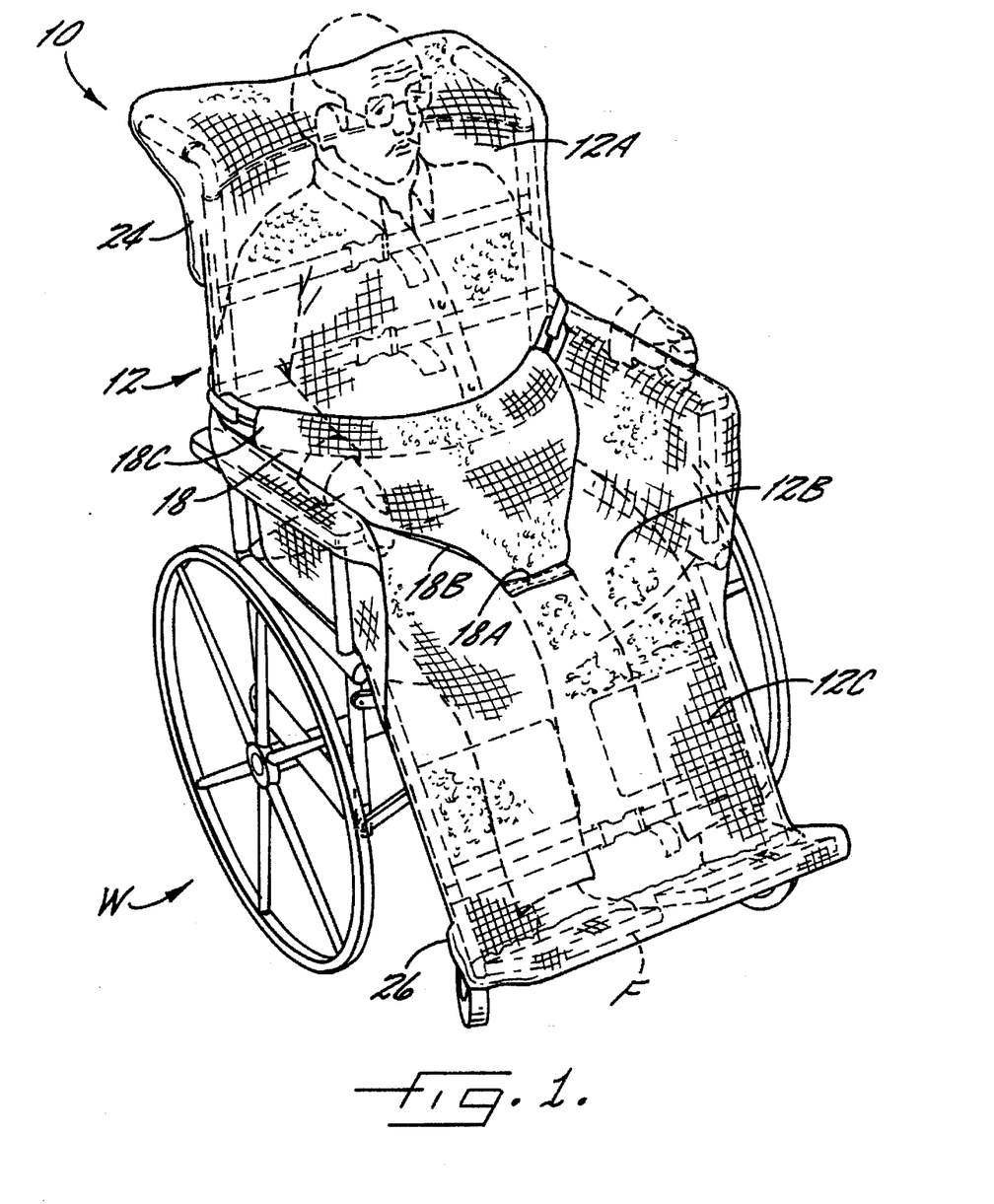
FIG. 1 illustrates a perspective environmental view of a restraint apparatus according to the present invention as it appears when secured to a wheelchair and supporting the lower torso of an infirm person.

The back section 12A, as shown for example in FIG. 1, is designed to be secured along the back portion of a chair or wheelchair and to extend between the chair and a user's back when the user is seated within the chair. The seat section 12B of the elongate body panel 12 is attached to the back section 12A, and is sized and configured to extend along the seat portion of a chair or wheelchair and beneath the lower torso, i.e. buttocks region, of a seated user. A leg section 12C extends from the seat section 12B of the elongate body panel 12, and is sized and configured to extend beneath the legs of a seated user. In a preferred form of the invention, the leg section 12C of the elongate body panel 12 has sufficient length to extend beneath a user's feet in the manner shown in FIG. 1. In this way, when the restraint 10 is secured to a chair, and particularly to a wheelchair W or geriatric chair G, it covers the foot supports F which form a part of the wheelchair. The leg section 12C of the elongate body panel 12 is thereby able to cradlingly support the feet of a wheelchair user and maintain the users feet in the desired position on foot supports F. The user's comfort is not only enhanced by the additional support provided, but the risk of injury is reduced since the risk of the user's feet falling from the foot supports F and in the path of the moving wheelchair W or geriatric chair G is reduced. Further, because the elongate body panel 12 extends beyond the edge of the seat of the chair and along the legs thereof, it helps prevent the seat edge from cutting into the underside of the restraint user's legs.

The restraint apparatus 10 also includes a lower torso panel 18, preferably having a lower end 18A secured to the seat section 12B of the elongate body panel 12 and a free upper end 18C. The lower end 18A of the lower torso panel 18 can be secured to the elongate body panel 12 using any conventional attachment method such as sewing, a zipper, or the like. Alternatively, the lower torso panel 18 can be secured by way of conventional releasable-type fasteners (not shown), such as hook and loop fasteners or snaps which, for example, can provide access to an adult's lower torso region such as for changing an adult diaper or other procedures where such access would be beneficial. Where releasable-type fasteners are utilized, a plurality of a first type of fastener can be provided along the elongate body panel 12 so that the user can select from a variety of staggered positions where the lower torso portion 18 is to be secured. In this way, the restraint apparatus 10 can be made to accommodate users of varying sizes and requiring varying amounts of support. The first lower end 18A of the lower torso panel 18 is preferably relatively narrow as compared with the free upper end 18C and the lower torso panel preferably is smoothly tapered between these upper and lower ends 18A and 18C along a tapered portion 18B. In this way, the narrow end 18A of the lower torso panel 18 can extend between a user's legs without causing discomfort to the user, and the tapered portion can conform smoothly to the contours of a user's body when the restraint apparatus is secured thereabout. Additionally, the lower torso panel 18 can be adjustably positioned, for example, from an upper position closely adjacent the underside of the user's arms to a lower position such as around the user's waist (see e.g., positions of panel 18 illustrated in FIGS. 1 and 5).

The restraint apparatus 10 includes a means for securing it to the desired upright seating support, i.e. chair, wheelchair W, geriatric chair G, automobile seat or the like. This means for securing the restraint apparatus to the seat is preferably in the form of an upper pocket 24, which is sized and configured to receive the back portion of a chair therein. This upper pocket 24 preferably extends across the full width of a rear side (i.e. the side opposite the one on which the user will sit) of the elongate body panel 12, preferably on the back section 12A thereof in order that it can accommodate chairs, i.e., preferably including the arms, of the same width as that of the elongate body panel. The upper pocket also desirably has sufficient size to enable it to receive the handlebars of a wheelchair and the headrest of a geriatric chair or automobile seat. In this way, the restraint apparatus also provides protective comfort for the hands of a person pushing the wheelchair, and a single restraint apparatus can selectively be used on a chair, a wheelchair, geriatric chair and an automobile seat, without the need for individual restraint devices for each place the person to be supported sits. Additionally, the enlarged size of the upper pocket 24 enables its easy removal from the wheelchair handlebars or automobile seat headrest in order that the restraint apparatus can be used as a stretcher for moving the person from the respective seat to another location. In a preferred form of the invention, the upper pocket 24 includes tightening means (not shown) about its open end for tightening the pocket 24 so as to provide a snug fit of the restraint apparatus to the chair back, particularly when the chair back is smaller than the restraint apparatus. A particularly preferred tightening means is a band of elastic material (not shown); however, other means such as a drawstring, hook and loop type fasteners, and the like can be used.

The restraint apparatus also desirably includes a lower pocket 26 proximate the leg section 12C of the elongate body panel. The lower pocket 26 is adapted, i.e. sized and configured, to receive the foot pedals of a wheelchair W, geriatric chair G, recliner or the like. The lower pocket 26 also desirably includes tightening means (not shown) about its open end in order to provide a snug fit of the restraint apparatus to the chair back, particularly when the chair back is smaller than the restraint apparatus. A particularly preferred tightening means is a band of elastic; however, other means such as a drawstring, hook and loop type fasteners, and the like can be used.

Figure 2:
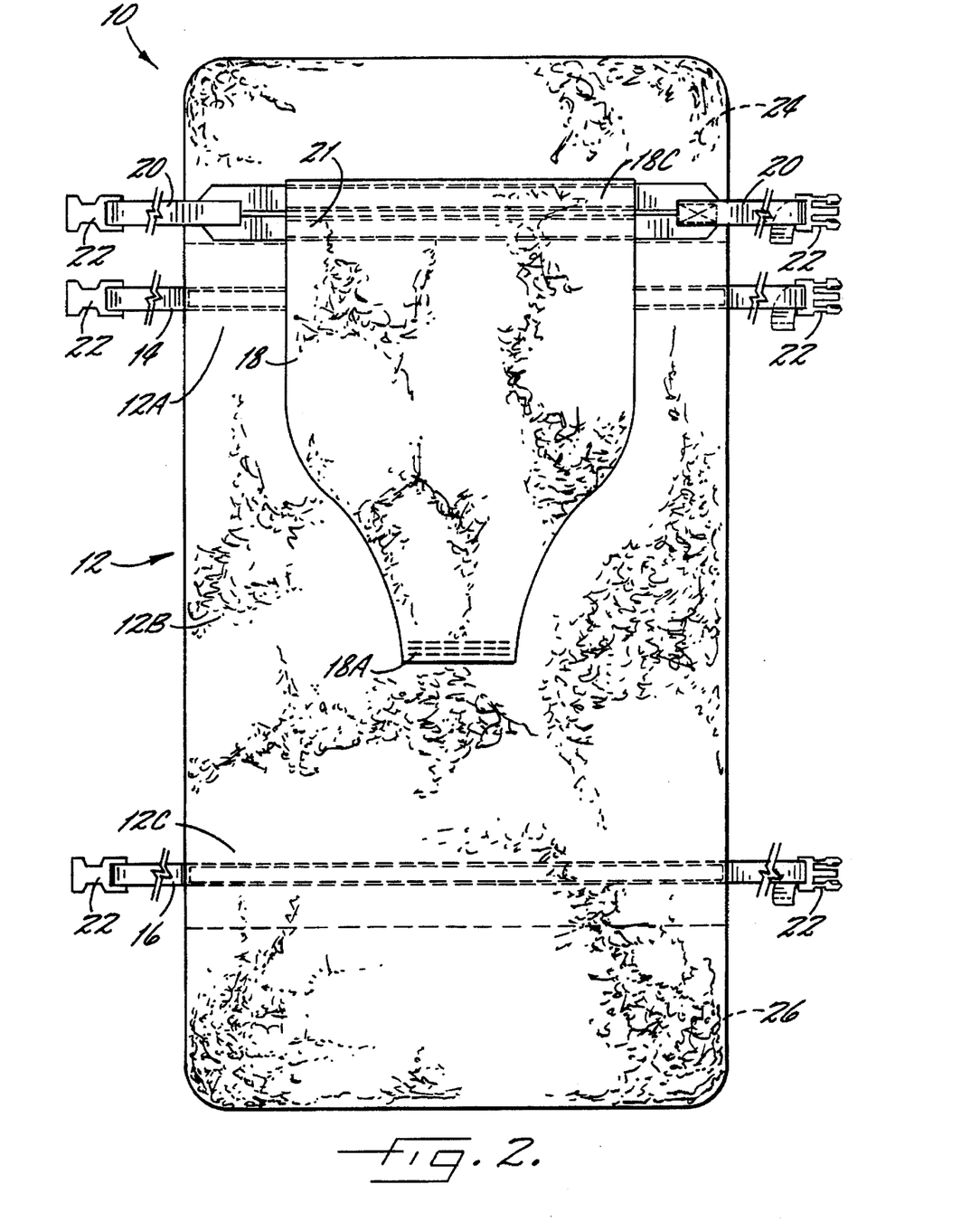
FIG. 2 illustrates a front plan view of an embodiment of a passive restraint apparatus according to the present invention.
Figure 3:
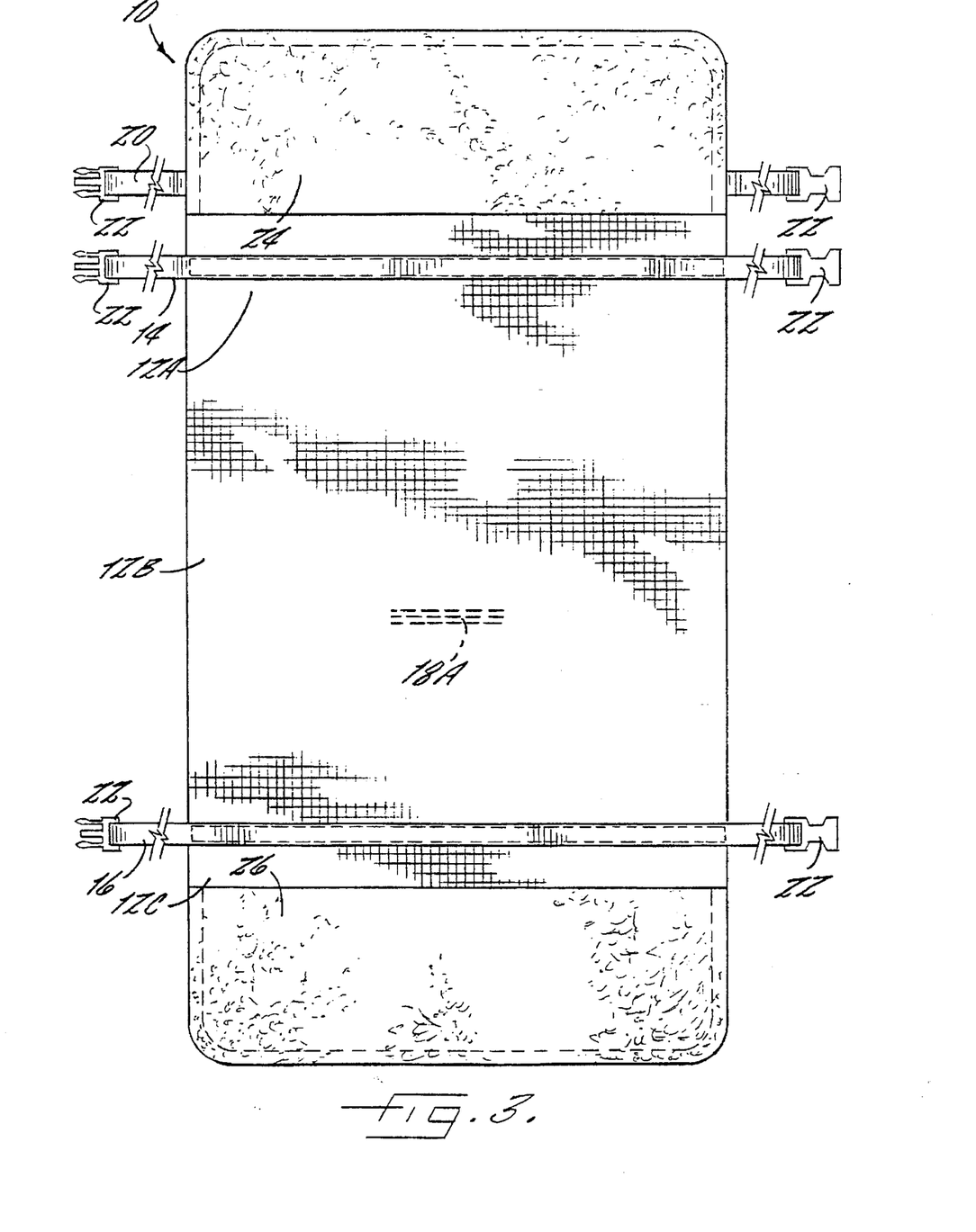
FIG. 3 illustrates a rear plan view of an embodiment of a passive restraint apparatus according to the present invention.

As shown more particularly in FIGS. 2 and 3, the restraint apparatus 10 preferably includes first and second pairs of mating straps 14, 16 for assisting in the securement of the restraint apparatus 10 to a chair or wheelchair. In a preferred form of the invention, one of the pairs of straps 14 is secured to the back section 12A of the elongate body panel 12 and another pair of straps 16 is secured to the leg section 12C of the elongate body panel 12. Each of the strap pairs 14, 16 can be formed using first and second individual straps or alternatively, the strap pair can be formed from a single piece of strap material which extends across the full width of the elongate body panel 12 in the manner shown in FIGS. 1 and 2.

In its preferred form, the restraint apparatus utilizes a single piece of strap material in this manner to form the strap pairs 14, 16, as the strap material extending across the width of the elongate body panel 12 provides added support to the restraint apparatus 10, which is particularly desirable when the restraint apparatus is used in the manner of a stretcher. The pairs of straps preferably include conventional mating fasteners 22 which enable the respective straps of the pairs 14, 16 to be secured together. In a preferred form of the invention, these mating fasteners are mating clips such as the types used on conventional backpacks, for example, which are threaded onto the straps 14, 16 in an adjustable manner. In this way, the effective length of the straps can be readily and simply adjusted to be snugly secured about chairs of various sizes. Thus, a single restraint apparatus 10 can be produced which can be used in combination with a large variety of shapes and sizes of chairs and wheelchairs. It is noted, however, that the fasteners 22 could be eliminated and the straps 14, 16 could be tied or otherwise secured together, though the use of adjustable fasteners provides a more comfortable and readily adjustable restraint apparatus.

Figures 4, 4A:
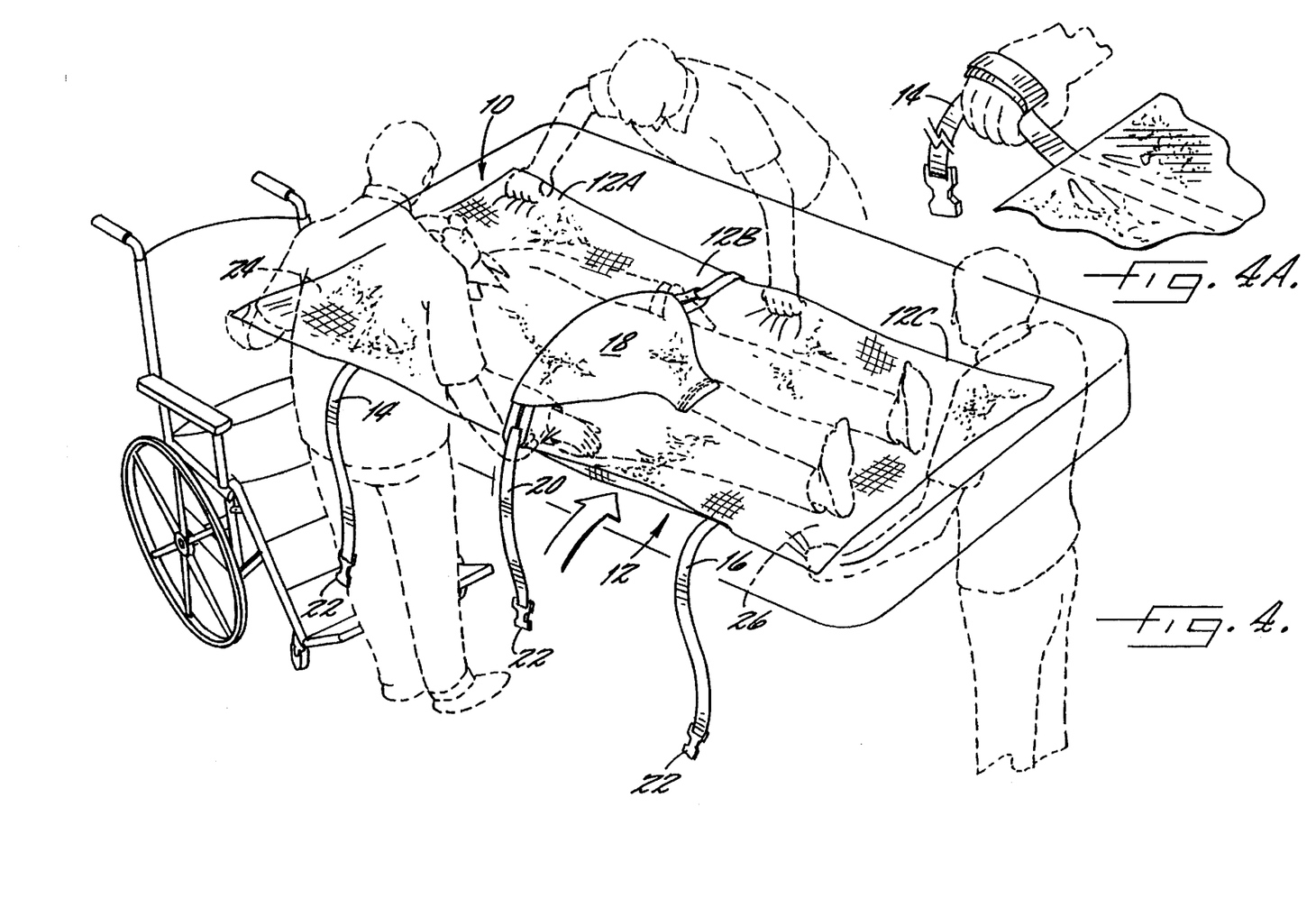
FIG. 4 illustrates a perspective view of a passive restraint apparatus according to the present invention being used to transport a user to a reclined position.
FIG. 4A illustrates an enlarged view of a portion of a restraint apparatus as shown in FIG. 4 having straps used by transporters to assist in carrying a person on thereon according to the present invention.

In the preferred embodiment of the invention, each strap forming the strap paris 14, 16 has a length sufficient to enable it to be grasped and/or wrapped around a transporter's hand in the manner shown in FIG. 4A. In this way, the straps 14, 16 serve the dual role of fastening the restraint apparatus to a chair and serving as handles when the restraint apparatus 10 is used to transport a person from one location to another. Additionally, supplemental handles (not shown) can also be provided to assist in the restraint's use in the manner of a stretcher.

A mating pair of straps 20 is also preferably secured to the upper end of the lower torso panel 18. This pair of straps 20, like the pairs of straps 14, 16, preferably includes a set of mating fasteners 22 which enables ready securement of the straps 20 together about a chair and user. The fasteners 22 and straps 20 are preferably adjustable in order that the effective length of the straps can be readily and easily adjusted in order that the restraint apparatus 10 can be used in combination with a variety of chair and user sizes and shapes. In addition, a portion of the lower torso portion 18 or the straps 20 could be made from a stretchable material which assists in achieving a snug fit of the lower torso portion 18 about a user and a chair. In a preferred form of the invention, a strap extends across the upper end of the lower torso panel 18 in order to provide support therefor. It is preferred that this strap have a width sufficient that it does not cut into the wearer's stomach. For example, the strap 21 can be made from two widths of the strap material used to form straps 20, since the same width would not be required for those straps not intended to contact the user's body. In addition, the upper end of the lower torso panel 18 can include padding to further enhance the comfort of the person being supported.

The elongate body panel 12 and lower torso panel 18 can be made from any of a variety of flexible sheet materials. Particularly preferred are fleece or pile-type materials such as synthetic sheep-skin or the like, as fleece and pile materials provide a degree of cushioning, thereby enhancing wearer comfort. Materials which can be laundered are particularly preferred, as they can be readily cleaned. It is noted, however, that any of a variety of materials can be used, such as vinyl, fabrics, mesh materials, etc., with the selection being made to enhance the user's comfort. Additionally, the restraint apparatus 10 can be made of non-stretch materials or somewhat stretchable materials though non or only slightly stretchable materials are preferred because they provide greater support to the user when the restraint apparatus 10 is used in the manner of a stretcher to transport the user from one location to another. Further, selected parts of the restraint apparatus 12, such as the seat section 12B and center of the back section 12A, can include supplemental padding to enhance the user's comfort. Alternatively, the entire device can be padded if desired.

Figure 5:
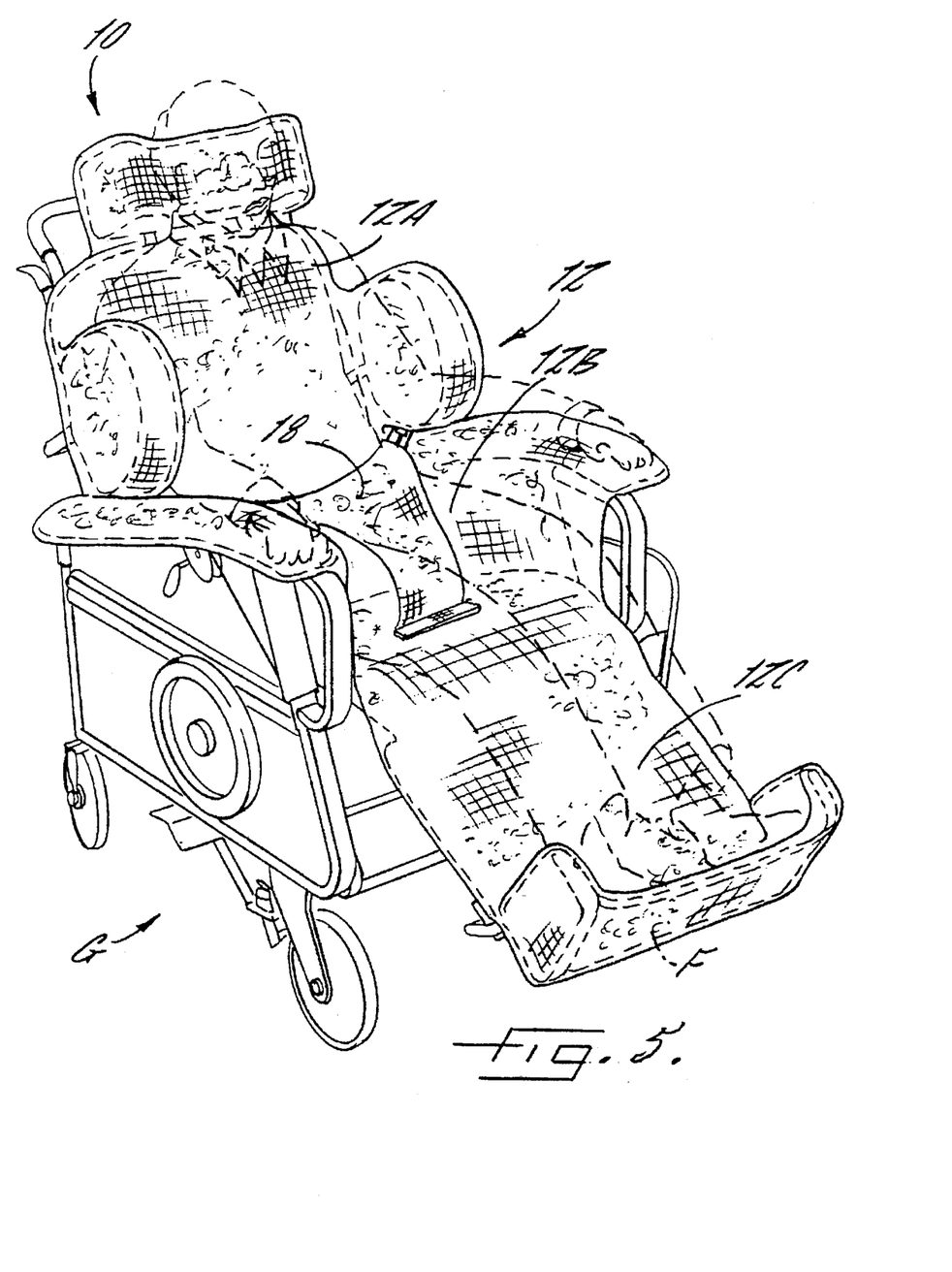
FIG. 5 illustrates a perspective environmental view of a restraint apparatus according to the present invention as it appears when secured to a geriatric chair and supporting an infirm person in a seated position.

The restraint apparatus is utilized as follows, and will be described as used in combination with a wheelchair W, as illustrated in FIG. 1, and a geriatric chair G, as shown in FIG. 5. It is noted, however, that the restraint apparatus 10 is used in like manner in combination with a conventional seat, chair, automobile seat, or the like. The upper pocket 24 of the restraint apparatus 10 is placed over the back of the wheelchair W or geriatric chair G in order that it envelopingly receives the upper portion of the wheelchair therein. The restraint apparatus 10 is then extended over the length of the wheelchair W so that it extends over the chair back, chair seat, and down to the foot supports F of the wheelchair W or geriatric chair G. The foot supports F are placed within the pocket 26 which is located proximate the leg section of the elongate body panel 12 forming the restraint apparatus 10. The pairs of mating straps 14 and 16 are then attached together proximate the back and underside of the wheelchair W or geriatric chair G, and their lengths are adjusted accordingly to ensure a snug fit of the restraint apparatus 10 about the chair.

The lower torso panel 18 is folded downwardly about its secured end 18A toward the foot supports F. The person to be supported in the wheelchair W then is seated in the wheelchair, and the lower torso panel 18 is brought upwardly through the person's legs so that the lower torso panel covers a portion of that person's lower torso. The straps 20 are brought together so that the lower torso panel 18 and straps encircle the user and the chair back, and the mating fasteners 22 are secured together. The effective lengths of the straps 20 are preferably adjusted either prior or subsequent to this securement, in order that the lower torso panel 18 is made to fit snugly but comfortably about the person being supported.

As illustrated in FIGS. 1 and 5, the upper torso of the person being supported is left unhindered; therefore, the person maintains free upper torso movement, enabling him or her to perform many activities despite being supported in the restraint apparatus. Further, because the restraint apparatus 10 is only visible on the front of the wearer about the lower torso region, the restraint apparatus can be obscured if desired by the placement of a blanket or lap robe on the wearer's lap. In this way, those persons who might find the necessity for a restraint apparatus to be a source of embarrassment can effectively hide their need for such in a simple and easy manner such as during travel in an automobile. In addition, because the restraint apparatus enables free and unhindered upper torso movement, the restraint apparatus remains comfortable to the user for extended periods of time. In contrast, more restrictive restraints may become a source of discomfort and anxiety.

The restraint apparatus 10 of the present invention has the additional utility of being usable for the easy transport of a person seated thereon. As illustrated in FIGS. 4 and 4A, the straps 14, 16, and 20 can be unfastened and the pockets 24 and 26 can be removed from the portions of the chair, wheelchair W, geriatric chair G, or the like which they cover. A plurality of transporters such as health center nurses can then seize opposite sides of the restraint apparatus 10 and extend it in the manner of a stretcher, while maintaining the person thereon. In this way, the person can be readily and easily transported to another location such as a bed or automobile seat without the need for the transporters to grasp the body of the person. Further, should the person being transported become uncooperative and attempt to kick or struggle, the transporters can bring the opposite sides of the restraint apparatus closer together to envelop the person being carried in a cocoon-like manner. In this way, the person is protected from injuring him or herself or the transporters.

The transporters can seize the sides of the elongate body panel 12 in the manner shown in FIG. 5, or can use the straps 14, 16 to assist in seizing the restraint apparatus in the manner shown in FIG. 4A. The strap pairs 14 and 16 perform particularly well when they are provided as single pieces of strap material which extend across the width of the elongate body panel 12, as this provides additional support for the person being transported. Additionally, where the straps 14, 16 are provided with sufficient length, they can be wrapped around the transporter's hands in the manner shown in FIG. 4A, to provide them with a surer grip of the restraint 12. Further, conventional handles (not shown) can be added as an alternative or supplement to the elongated straps 14, 16 to assist in the use of the restraint apparatus 10 as a transporting stretcher type device.

As illustrated in FIGS. 1, 4, 4A, and 5, the present invention also includes a method for passively restraining a patient in a seated and upright position. The method preferably includes positioning an elongate body panel so as to extend over a back portion, a seat portion, and a lower leg portion of a chair. The chair may also include foot supports connected to the lower leg portion of the chair. A lower pocket connected to the lower end portion of the elongate body panel is positioned so as to extend over the lower end portion and/or the foot supports of the chair. The method also includes positioning a patient on the elongate body panel in the chair and securing the patient to the chair by positioning a lower torso panel connected to the elongate body panel such that a first end of the lower torso panel is secured to the elongate body panel between the patient's legs and a second end is secured around the lower torso of the patient and to the chair proximate the back section of the restraint apparatus to thereby support the patient within the chair.

In the drawings and specification, there have been disclosed typical preferred embodiments of the invention and, although specific terms are employed, these terms are used in a descriptive sense only and not for purposes of limitation. The invention has been described in considerable detail with specific reference to various illustrated embodiments. It will be apparent, however, that various modifications and changes can be made within the spirit and scope of the invention as described in the foregoing specification and defined in the appended claims.

What is claimed is:

1. A passive restraint apparatus for supporting a user thereof in a substantially upright seated position in a chair so as to allow free upper torso movement of the user, the restraint apparatus comprising:

an elongate body panel including a back section adapted and configured to extend along a back portion of a chair, a seat section connected to the lower end portion of said back section and adapted to extend along a seat portion of a chair, a lower leg section connected to the lower end portion of said seat section for extending downwardly from a seat portion of a chair and along a lower leg portion thereof, arm sections connected to and extending outwardly from said seat section and adapted to connected to said back and lower leg sections for covering arms of a chair and inhibiting a user's interference with the arms of a chair, and wherein said elongate body panel has a substantially constant width along said back, seat, arm, and lower leg sections, and a foot section connected to the lower end portion of said lower leg section and adapted to extend along foot supports connected to and extending outwardly from a chair;

means connected to said elongate panel for securing said elongate body panel to a chair; and a lower torso panel secured to and extending outwardly from said elongate body panel for positioning between the legs of and around the lower torso of a user, said lower torso panel including means for securing said lower torso panel around the lower torso of the user and around a back of a chair.

2. A restraint apparatus according to claim 1, wherein said means for securing said elongate body panel to a chair comprises an upper pocket connected to the upper end portion of said back section of said elongate panel, said upper pocket being sized to envelopingly receive a portion of a back of a chair, and a lower pocket connected to said foot section and said lower leg section of said elongate body panel, said lower pocket being adapted to receive foot supports and a lower leg portion of a chair to secure the restraint apparatus thereto and inhibit a user's feet from interfering with foot supports of a chair.

3. A restraint apparatus according to claim 2, wherein said means for securing said elongate body panel further comprises a plurality of elongate straps extending across the width of said elongate body panel and secured thereto to thereby provide structural support to the elongate body panel when lifting a user positioned on said elongate body panel, at least one of said plurality of elongate straps being secured to said back section of said elongate body panel and at least one of said plurality of elongate straps being secured to said leg section of said elongate body panel for more stably lifting a user positioned thereon.

4. A restraint apparatus according to claim 3, wherein said lower torso panel further includes a first relatively narrow end connected to a medial portion of said lower torso panel and a second relatively wider end tapering and extending outwardly therefrom, and wherein said securing means includes an elongate strap secured to the relatively wider second end and adapted to extend around a user positioned therein and around a back of a chair.

5. A restraint apparatus according to claim 4, wherein said plurality of straps extend outwardly a substantial length beyond said elongate body panel when not secured to a chair and for also forming a plurality of handles secured to said elongate body panel for lifting a user when positioned on said elongate body panel.

6. A combination of a wheeled chair having foot supports and a restraint apparatus for supporting a person in a seated upright position thereon, the combination comprising:

a wheeled chair including a back portion, a seat portion connected to said back portion, a leg portion connected to said seat portion, and foot supports connected to said leg portion and extending outwardly therefrom for supporting the feet of a user positioned thereon; and a restraint apparatus, said restraint apparatus including a back section secured to the back portion of said wheeled chair, a seat section extending along the seat portion of said chair, and a lower leg section extending from the seat portion of said chair to said foot supports and secured about the foot supports to thereby provide cradling support for the legs and feet of a person seated in said chair, and a lower torso panel secured to the seat section of said restraint apparatus for extending between the legs of a user positioned in said chair and supporting the lower torso of a user positioned thereon.

7. A passive restraint apparatus for supporting a user thereof in a substantially upright seated position in a chair so as to allow free upper torso movement of the user, the restraint apparatus comprising:

an elongate body panel including a back section adapted to extend along a back portion of a chair, a seat section connected to the lower end portion of said back section and adapted to extend along a seat portion of a chair, a lower leg section connected to the lower end portion of said seat section for extending downwardly from a seat portion of a chair and along a lower leg portion thereof, and a foot section connected to the lower end portion of said lower leg section and adapted to extend along foot supports connected to and extending outwardly from a chair;

means connected to said elongate panel for securing said elongate body panel to a chair, said securing means comprising an upper pocket connected to the upper end portion of said back section of said elongate panel and being adapted to envelopingly receive a portion of a back of a chair, a lower pocket connected to said foot section and said lower leg section of said elongate body panel and adapted to receive foot supports and a lower leg portion of a chair to secure the restraint apparatus thereto and inhibit a user's feet from interfering with foot supports of a chair, and a plurality of elongate straps extending across the width of said elongate body panel and secured thereto to thereby provide structural support to the elongate body panel when lifting a user positioned on said elongate body panel, at least one of said plurality of elongate straps being secured to said back section of said elongate body panel and at least one of said plurality of elongate straps being secured to said leg section of said elongate body panel for more stably lifting a user positioned thereon; and a lower torso panel secured to and extending outwardly from said elongate body panel for positioning between the legs of and around the lower torso of a user, said lower torso panel including a first relatively narrow end connected to a medial portion of said lower torso panel, a second relatively wider end tapering and extending outwardly therefrom, and torso panel securing means for securing said lower torso panel around the lower torso of the user and around a back of a chair, said torso panel securing means including an elongate strap secured to the relatively wider second end and adapted to extend around a user positioned therein and around a back of a chair.

8. A restraint apparatus according to claim 7, further comprising an upper pocket attached to upper end portions of said back section of said elongate body panel, said upper pocket being adapted to receive upper end portions of a back of a chair therein.

* * * * *